United States Patent [19]
Muller et al.

[11] 3,934,731
[45] Jan. 27, 1976

[54] APPARATUS FOR INSPECTING AND REPAIRING A PRESSURIZED-WATER REACTOR'S STEAM GENERATOR HEAT EXCHANGER TUBES

[75] Inventors: Otto Müller, Spardorf; Hans Röttger, Weiher; Hans Kastl, Neustadt, a.d. Waldnaab; Hans-Günter Hagen, Erlangen, all of Germany

[73] Assignee: Siemens Aktiengesellschaft, Munich, Germany

[22] Filed: Dec. 20, 1973

[21] Appl. No.: 426,483

[30] Foreign Application Priority Data
Dec. 22, 1972  Germany............................ 2264143

[52] U.S. Cl................ 214/1 BB; 165/76; 214/1 CM
[51] Int. Cl............................................. F28g 15/02
[58] Field of Search............ 214/1 BB, 1 BC, 1 CM; 165/76

[56] References Cited
UNITED STATES PATENTS
| | | | |
|---|---|---|---|
| 3,643,701 | 2/1972 | Wadiak................................ | 165/76 |
| 3,811,320 | 5/1974 | Cowell............................. | 214/1 CM |

*Primary Examiner*—Robert J. Spar
*Assistant Examiner*—George E. Abraham
*Attorney, Agent, or Firm*—Kenyon & Kenyon Reilly Carr & Chapin

[57] ABSTRACT

An apparatus is provided for use with a pressurized-water reactor's steam generator having a manifold chamber enclosing the bottom side of a horizontal tube sheet having holes therethrough in which are mounted the tubes of a heat exchanger tube bundle, the manifold chamber having a manhole giving access to the tube's bottom side to permit internal inspection or repair of the tubes by registration of an end of a flexible guide conduit with the tube sheet holes and through which a flexible carrier can be guided for insertion via these holes in the tube sheet and through the tubes extending from the tube sheet's other side. The apparatus is a light-weight fixture which is manually insertable through the manhole and comprising a beam, means for detachably supporting the beam horizontally in the chamber beneath the tube sheet's bottom side, a horizontal cantilever arm having one end provided with means for supporting the aforementioned guide conduit with its end pointing upwardly and means for mounting the other end of the arm on the beam for horizontal movement of its end having the guide conduit supporting means. The carrier is a flexible hose insertable through any one of the heat exchanger tubes, and being tubular, the carrier hose can carry conductors from an inspection or repair device mounted on the inner end of the carrier hose, back to the relatively safe, remote location for measuring or controlling purposes. The apparatus has additional features.

9 Claims, 6 Drawing Figures ific steam generator heat exchanger tubes, but other appropriate uses involving analogous problems are included in the inventive concept.

APPARATUS FOR INSPECTING AND REPAIRING A PRESSURIZED-WATER REACTOR'S STEAM GENERATOR HEAT EXCHANGER TUBES

BACKGROUND OF THE INVENTION

A steam generator for a pressurized-water nuclear reactor, comprises a cylindrical upstanding housing having a steam output outlet at its top and provided with a feed-water inlet, the bottom of the housing being closed by a horizontal tube sheet of cylindrical contour. An upstanding, inverted U-shaped heat exchanger tube bundle has its inlet and outlet legs, each comprising a multiplicity of tubes and defining a generally semicylindrical cross-sectional contour, mounted in holes formed in the tube sheet. A hemispherical enclosure below the tube sheet has a vertical partition separating it into inlet and outlet manifolds, respectively provided with inlet and outlet water-coolant connections, defines inlet and outlet chambers for the holes opening through the tube sheet and in which the heat exchanger legs are mounted. Within each of these chambers the cross-sectional contour adjacent to the tube sheet is of a generally semi-circular contour and cross section.

In operation, water coolant from the pressurized-water reactor is circulated through the heat exchanger via the inlet and outlet manifold chambers. The water coolant picks up radiation activity from the reactor and transfers it to these chambers and with time these chambers become active to a degree which is dangerous to a workman who might enter either chamber when empty, and remain there far too long a time.

Using either of the chambers as an example, it is provided with a manhole which, when opened, permits a workman to enter the chamber, the latter being empty and the reactor normally being in a shut-down condition during such time. A workman must enter this chamber whenever the heat exchanger tubes are to be internally inspected or repaired because such work must be done via the bottom ends of the tubes and their holes through the tube sheet.

It is possible to make such inspection and repair by the workman entering the chamber, by attaching the end of a flexible guide conduit to the tube sheet at the hole of the tube to be inspected or repaired. After such attachment, the workman may leave the chamber and from a safer location a flexible carrier hose can be inserted via this guide conduit into the heat exchanger tube. The carrier hose may carry on its inserted end various devices for either inspection or repair, as by plugging the tube involved. This procedure must be repeated as to each of the heat exchanger tubes, thus subjecting the workman to an undesirably prolonged exposure to the radiation activity persisting within the chamber.

It is apparent that the foregoing presents a problem requiring a solution.

SUMMARY OF THE INVENTION

The object of the present invention is to provide such a solution.

According to the invention, a light-weight fixture is provided which the workman can carry into the chamber via the manhole, and organize in a detachable manner, this fixture supporting the end of the flexible guide conduit which is also carried into the chamber, and being motorized and constructed in such a fashion that from a safer remote position, by remote control there, the carrier hose can be moved into registration with any one of the openings of the tube sheet, and with each registration the carrier hose may be used for inspection and repair of that tube. The workman is required to enter the chamber only twice, once to install the fixture and once to remove the fixture, thus greatly reducing his exposure time to the radiation activity in the chamber.

Briefly stated, this fixture comprises a beam having means on its ends for pressing against the chamber's walls adjacent to the linear portion of the semi-circular group of hole openings through the tube sheet. This beam has a longitudinal guideway mounting a primary cantilever carriage extending transversely from it towards the curve side of the chamber, and a motor is provided for causing this arm to traverse the beam. This carriage, in turn, has a longitudinal guideway extending from its end on the beam guideway and transversely with respect to the latter, and a secondary carriage is mounted by this guideway to travel therealong, a second motor being provided to effect this traverse of the arm. This secondary carriage pivotally mounts one end of a horizontally swinging cantilever arm and which is also provided with a motor for effecting this swinging.

With the above construction, with the three motors remotely controlled, the swinging end of the arm mounted by the secondary carriage, which can be moved back and forth on the primary cantilever carriage, can be moved to register beneath the tube sheet with any one of the latter's heat exchanger tube openings, this swinging end being capable of traversing all of the clustered group of holes.

Therefore, by providing the swinging end of this arm with means for mounting the flexible guide conduit end, the latter may be moved into registration with any one of the holes from the safer remote location where suitable control equipment may be located. The electric control systems prior art is adequate to permit the design of the various motors and the remote control equipment to provide for programming whereby with a known pattern and interspacing of tube sheet hole openings, the fixture can be used to register the guide conduit end with any one of the holes, the fixture including means for initially centering it within the manifold chamber beneath the tube sheet, when installed.

The flexible carrier hose inserted via the guide conduit into the heat exchanger tubes may carry inspection devices and tools of various kinds on an inner end with, when necessary, conductors being carried through the inside of the conduit back to the control location. For example, the device may be an electric eddy current probe for measuring the tightness and integrity of the tube, permitting detection of even small leaks or cracks in the tube inspected. This requires conductors running back through the inside of the carrier hose. Continuity of a tube can be checked by sending compressed gas through the inside of the carrier hose, and this may also be done for tube cleaning, and in this instance, the conductors running through the tube are not required. Another example of the latter is the use of compressed gas sent through the carrier hose to activite a rotary brush passed through the heat exchanger tube by being mounted on the inner end of the carrier hose.

If the tube being inspected is found to be defective, it may be put out of service by closing off its defective portion by explosively expandable metal plugs inserted at appropriate locations via the carrier hose, such a plug requiring electric ignition wires to extend back to the location via the inside of the carrier hose.

At the control location, a number of reels, each carrying an adequate length of carrier hose, each having on its inner or working end a different kind of inspection or repair device. At this relatively safe location, any one of the reels may be used to feed its carrier hose through the flexible guide conduit, the latter being provided with powered means for pushing and pulling the hose through the conduit as required for it insertion and removal in the heat exchanger tube involved. The linear travel of the hose may be measured so that the position of any fault or defect in the tube can be determined. The location of such a fault being known, repair measures may be taken either in the direction of cleaning or plugging, the reel carrying the hose used for measuring the defect reeling the measuring hose back and being removed, with another reel carrying the hose with the repair or plugging device being substituted and then used to carry the device to the detected location of trouble. At its location the control may comprise a suitable control console carrying positioned detecting and condition measuring equipment.

A pressurized-water nuclear reactor power plant facility includes an electronic computer for controlling the reactor operations, and such a computer ordinarily has a substantial unused capacity. The apparatus of the present invention may feed information to this computer for storage and retrieval, sequential operation of the motorized fixture to permit inspection of one heat exchanger tube after another, storage of information concerning the tube inspected and the location of any located fault, etc. Also, the computer may be used to activate the control console as required to perform the various functions previously suggested, this being of advantage because the computer is customarily located in a room entirely free from radiation activity. Using the computer, a workman needs to be present at the control console only long enough to change the reels of carrier hose, it being assumed that although the location of this console, which may be portable, is relatively safe, it may still be somewhat close to the steam generator and exposed to some activity, which, however, should not be anything like so intense as exists within the manifold chamber of the steam generator.

BRIEF DESCRIPTION OF THE DRAWINGS

An example of the invention is schematically illustrated by the accompanying drawings, in which.

DETAILED DESCRIPTION OF THE INVENTION

Figure 1:
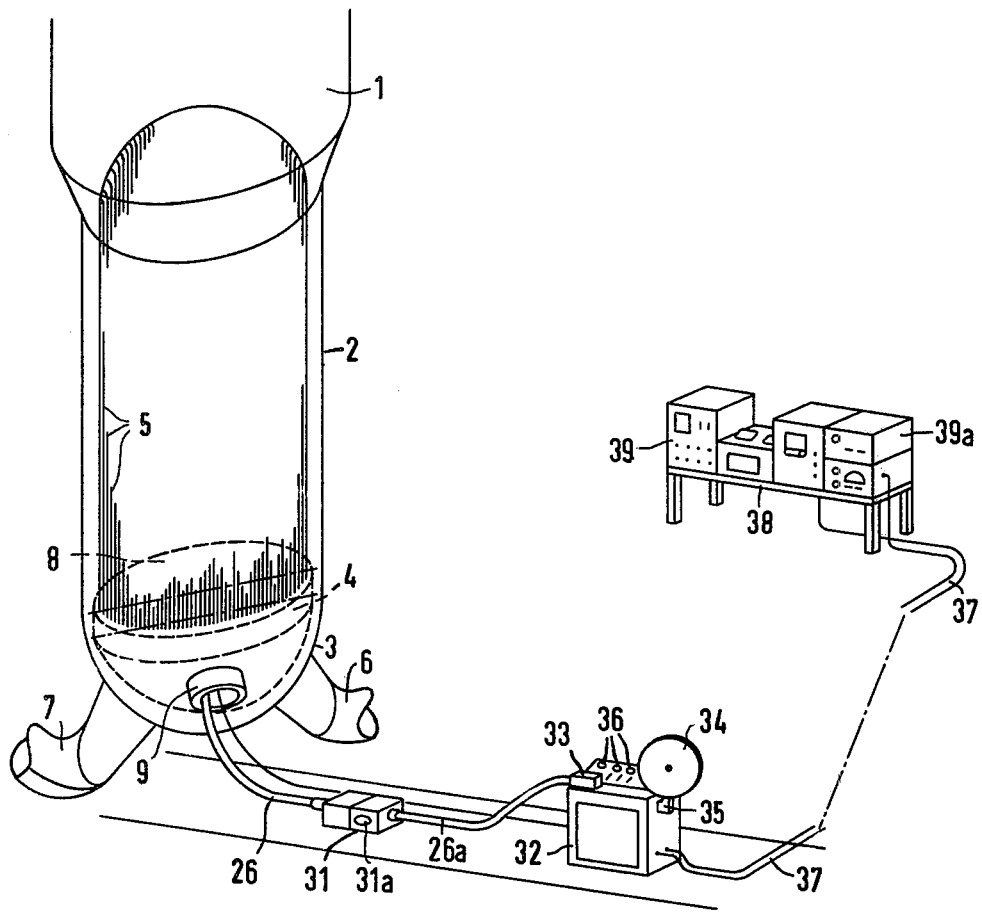
FIG. 1 is a simulated perspective view showing the steam generator for a pressurized-water reactor with the tube bundle shown schematically in phantom.

FIG. 1 representatively illustrates the steam generator comprising a housing forming a steel dome 1 in the top of which the steam output is located, and beneath which a cylindrical housing 2 extends vertically to a hemispherical bottom wall 3 which forms one of the previously mentioned manifold chambers, the bottom of the cylindrical housing portion 2 being closed by a horizontal tube sheet 4 from which the inverted U-shaped tube bundle extends upwardly into the portion 2 with its individual tubes indicated at 5 having their lower ends positioned in the holes formed in the tube sheet 4. The inlet and outlet legs are supplied via the manifolds by an inlet connection 6 and an outlet connection 7. The two legs of the tube bundle are not specifically illustrated, but the broken line 8, shown as extending across the top of the tube sheet 4, indicating the center line or plane dividing the two vertical tube bundle legs. The manhole or manifold chamber access opening is shown at 9.

This FIG. 1 is intended only for illustrative purposes, the details of the construction of the described type of steam generator being well known industrially. The manhole 9 is necessarily offset horizontally from vertical alignment with the bottom ends of the tubes and their holes through the tube sheet, this making it necessary to use the flexible guide conduit containing the flexible carrier hose previously referred to. It is to be understood that the inside diameter of the guide conduit is substantially the same as the inside diameter of the heat exchanger tube bundle tubes, that the carrier hose has an outside diameter that is smaller and that any device to be inserted through the bottom of the tube sheet into the heat exchanger tubes must have a diameter permitting its insertion in the latter.

Figure 2:
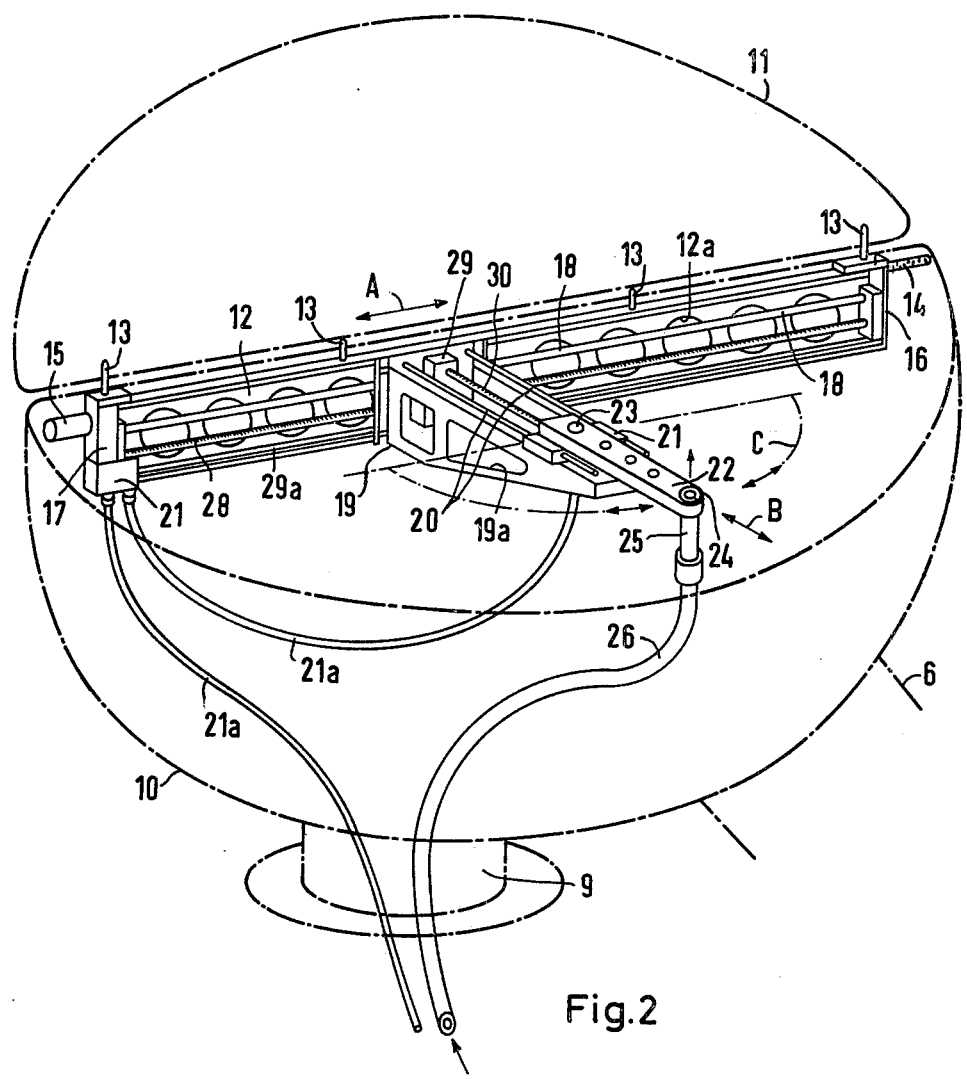
FIG. 2 is a simulated perspective view of the fixture.

The new fixture is illustrated by FIG. 2 installed in the inlet manifold chamber, the outline of which is indicated by the broken line 10, the contour of the other or outlet manifold being indicated by the broken line 11. In this way the semi-circular cross-sectional contour of the upper portion of the manifold chamber beneath the bottom of the tube sheet is illustrated as to both manifold chambers, the fixture in this instance being installed in the inlet manifold. The pressurized-water coolant delivered from the reactor is at its highest temperature while going through the inlet leg of the tube bundle so that the tubes of this leg operate under the maximum thermal stress to which the heat exchanger is subjected.

THe fixture includes the beam 12 which is made as light as possible as is consistent with structural rigidity, the beam being in the form of a channel having weight-reducing holes 12a formed in its web and being made of relatively light-gauge metal. To center the fixture, the beam has upstanding pins 13 adapted to enter holes (not shown) formed in the bottom of the tube sheet 4 prior to the steam generator being put into operation. At one end the beam has a horizontal pin 14 which by manual screw adjustment may be extended to press against the inside of the manifold chamber, while at the other end of the beam there is a horizontal extensible member 15 which may, for example, be of the pneumatic type and which serves to press against an opposite side of the manifold chamber so that the beam can be frictionally retained and positioned up close to the tube sheet horizontally inside of the flat side of the semi-circular pattern of tube holes in the tube sheet.

The beam 12 has vertical members 16 and 17 extending between its upper and lower flanges and which mount the previously referred to guideway in the form of a guide rod 18 extending between these members 16 and 17 in parallel relationship to the beam.

The primary cantilever carriage 19 slidably rides on this guideway 18, so as to traverse the beam substantially from one of its ends of the other, this carriage extending from the beam for a substantial distance and at a right angle to the beam. The cantilever construction of this carriage 19 is also made as light in weight as is consistent with structural rigidity, its side walls tapering to the end away from the beam and having weight-reducing openings 19a. The top of this cantilever carriage mounts a guideway in the form of laterally interspaced mutually parallel bars 20 in which the secondary carriage 21 slidably rides back and forth at a right angle to the traversing direction of the secondary carriage 19 with respect to the beam 12. This carriage is removable from the beam.

It is this secondary carriage 21 that carries the horizontal swinging arm 22 by having its end connected to the carriage 21 by a rotating shaft 23 keyed to that end of the arm 22. The arm swings as a cantilever about this shaft 23 in the horizontal direction and its swinging end 24 has the connection 25 by which the end of the flexible guide conduit or tube 26 is connected to this arm end 24. This connection 25 is tubular and provides an inside diameter the same as the inside diameter of the flexible guide conduit 26.

A miniaturized electric motor 27 of the reducing gear type rotatively drives a screw-threaded drive shaft 28 journaled between the beam's end member 16 and 17, and which is in screw-threaded engagement with the carriage 19. In this way the primary cantilever carriage 19 is motorized for the horizontal transverse motion back and forth indicated by the arrow A. The secondary carriage 21 mounted by the primary carriage 19 has a corresponding type of motor 29 to effect its right angular traverse in the direction of the arrow B via a screw-threaded drive shaft 20 which is in screw-threaded engagement with this secondary carriage 21. This secondary carriage itself, as a part of its construction, carries a third motor of the type described which drives the shaft 23 which both supports the swinging arm 22 and is keyed to it to swing it in the direction of the arrows C.

The three motors described above have been suggested as being electric motors. Other types may be used. To enjoy the advantages of the invention, each of the three motors should be capable of being remotely controlled to effect the motions A, B and C for positively determined extents known to register the swinging end of the arm 22 carrying the conduit connection 25 into registration with each of the tube holes in the tube sheet. Motors of suitable types are known in the automated control systems art.

The motor 27 is connected to a flexible power line 27a which may be, for example, of the multi-conductor type in case the motors are of the electrically powered type, and within the housing of the motor 17, through another circuit, connected by a flexible conductor 21a with the motorized carriage 21, another branch circuit powering a suitable conductor rail 20a which is provided for the motor 29 which via sliding contactors picks up its power via these conductor rails. The conductor 27a, if of the multi-conductor type, can carry the three individual circuits for the three motors away via the manhole 9 through which the fixture is inserted and removed and through which the flexible guide conduit 26 is also passed.

With the fixture carried into the manifold chamber via the manhole by the workman and installed as described, reference may now be made back to FIG. 1 where the flexible guide conduit 26 is shown as extending from the manhole 9 to an end connected with a transport hose feeding device 31 powered by a motor 31a and which may contain, for example, pinch rolls (not shown) engaging the carrier hose and powered by the motor 31a. From this feeding device 31 another section of guide conduit 26a extends to a control console 32 where the end of this section 26a is connected to a carrier hose insertion box 33 mounted on the top of the console. One of the previously referred to reels on which one of the carrier hoses is stored in coil form, is indicated at 34 supported by the console 32 via an upstanding branch arm 35 through which the reel 34 is removably attached. As previously indicated, there may be a number of these reels 34 each carrying a coil of the carrier hose with a different device on the insertion end of each hose. In the case of the reel 34 the hose would have its insertion end inserted in the insertion box 33 and pushed forward manually or the insertion box 33 may contain a drive, although this is not indicated, to the feeding device 31 where the motor 31 a then applies the feeding force both to feed and remove the insert hose used in the heat exchanger tube. The multi-conductor cable 27a from the fixture goes via the manhole 9 to the control console where the latter is indicated as having three control buttons 36 for actuating the three motors of the fixture. Preferably a control system is provided so that actuation of any one or combination of the control buttons actuates the fixture's motors to move the guide connection 25 to a next successive one of the tube openings of the tube sheet. The reel 34, and the other reels, should be provided with an internal connection for the end of the transport hose for obtaining signals from conductors in the latter, supplying it with compressed gas and the like. Such signals may be read directly by installations at the console 32 or as previously indicated, fed via conductors 37 to a control station 38 located in the power plant's control room entirely free from radiation hazards. The console 32 would normally be positioned reasonably remote from the steam generator where the radiation hazard is substantially less than exists within the steam generator's manifold chamber.

This control station 38 includes, among other things, equipment 39 for recording measured data, for example, via magnetic storage, as well as an operating controller 39a which permits exact control of the three motors of the fixture, which may here be done by computerized electronic circuitry. Control lights and the like may be used here to indicate the operation of individual tools motors, and position of devices in any one of the heat exchanger tubes, and the like.

The suggested use of the new apparatus is as follows:

It is to be assumed that previously the apparatus has been used to obtain results from an eddy current test of the tubes, the results having been stored in a suitable memory such as by the equipment at the station 38. This information includes the heat exchanger tubes having suspected defects, these being marked exactly on an overall plan (for each of the steam generators of the plant) and the sequence of the approach to the various tube positions advantageously set before any repair work begins.

The various tube positions are once more subjected to an eddy current test to obtain a new recordal which can be compared to the results of the first measurements.

Figure 3:
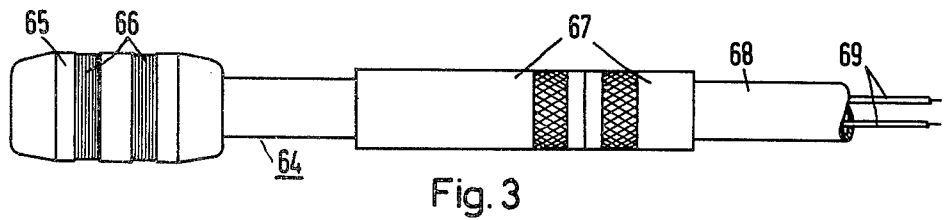
FIG. 3 is a side view showing an electric eddy current probe attached to the end of a carrier hose, this and the device illustrated by the following figures having a suitable diameter for insertion in the heat exchanger tube.

A suitable test probe is shown by FIG. 3 as including a testing head 65 with coils 66 supported by a connector 67 with a flexible transport hose 68 carrying conductors 69 which via the hub of the reel 32, or any of the other reels on which the hose 68 is coiled, go to installation and recording arrangements. The coils 66 are, of course, energized with alternating electric current to make the test. After this test, the hose 68 via the feeding device 31 is withdrawn and recoiled on its reel and another reel with a compressed air motor and cleaning brush on its ends is inserted via the insertion device 33 for ultimate insertion, using the fixture, into the tube measured and possibly found to need repair.

Figure 4:
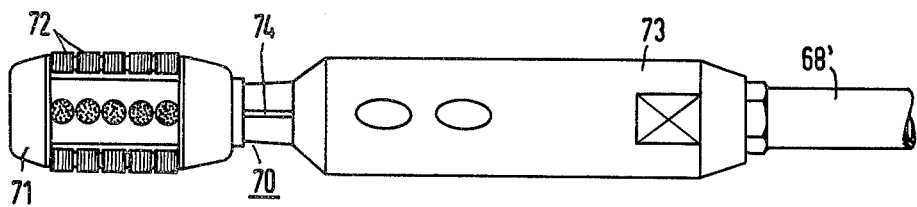
FIG. 4 is a side view of a rotative cleaning brush attached to another carrier hose.

FIG. 4 shows the cleaning brush 70 having the rotating brush head 71 with bristles 72 fixed in movable segments, the bristles being pushed outward when a compressed air motor 73 revolves the segments and the bristles via the drive shaft 74, in this instance compressed air being supplied via the carrier hose shown here at 68'. After this brushing operation of the area to be repaired within the heat exchanger tube, this hose 68' is then recoiled on its reel and the latter removed. Such cleaning brush operation need only occur for about twelve to fifteen seconds.

Figure 5:
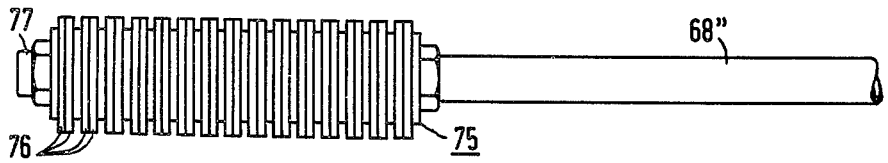
FIG. 5 is a side view showing a scouring plug attached to the end of still another carrier hose.

The next reel with a scouring plug 75 as the tool is placed on the mounting 35 and secured. The scouring plug includes as shown in a side view in FIG. 5, flexible washers 76 fitting the inside diameter of the tube, which are clamped on a bolt 77 which is fastened to the end of this transport hose 68'. The scouring plug 75 is inserted into the opening of the guide conduit 26a, being moved manually to the vicinity of the insertion device 33, and thereby releases an indication at the console 50. The scouring plug 75 is pushed into the heat exchanger tube up to the stop position and then pulled out of the tube. It is subsequently pulled out of the conduit 26a and is recoiled on its reel.

Figure 6:
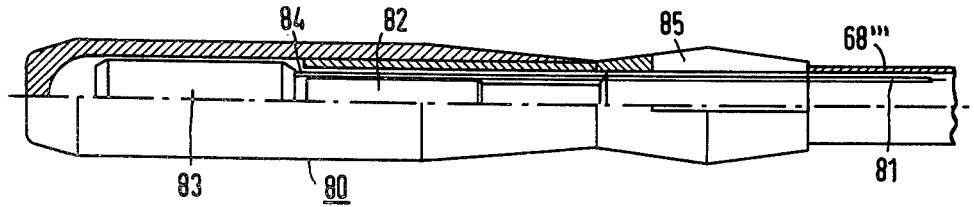
FIG. 6 is a side view of an explosively expandable metal plug attached to the end of still another carrier hose.

Then, the size of a sealing plug 80 is determined, which is shown in FIG. 6 partly in cross section. The reel with prepared carrier hose 68''' and cables 81 situated therein, is placed on the mounting 35 and secured. The complete sealing plug 80 of defined diameter is taken from a supply container, is equipped with a primer 82 and detonator capsule 83, and the two ignition cables at 84 are securely connected with each other, together with the cables 81 in the carrier hose 68''' via a special connection in the region of the plug sleeve 85.

The sealing plug 80 is inserted by hand into the insertion device 33 and is moved up to the tube connection 25 where the indication at the console 50 takes place again. The plug is then pushed into the heat exchanger tube until a stop at the conduit feeder 31 indicates the required depth in the tube. The transport hose 68''' is pulled out of the tube again and the arm 22 is advanced by several tube pitches, so that the tube end is definitely free. The cable ends 81 protruding from the opposite tubing end at the reel are connected to the ignition equipment, whereby the ignition is prepared.

Through the ignition the ignition cables are sheared off and the sealing plug 80 is securely fastened in the tube.

After the work in the chamber is completed, the fixture of FIG. 2 is removed. To this end, the primary carriage 19 is run into a position favorable for disassembly and the arm 22 is set to the row of tubes next to the beam 12. Prior to the removal, the various supply elements are disconnected at the control console 32.

A man climbs into the chamber through the manhole 9 and disconnects the conduit 26 from the arm 22, and deposits it at the bottom. The primary carriage 19 is caught with one hand, at its end, is swung into an oblique position after loosening of locking devices and is lifted out and is passed through the manhole to a second man and is carefully laid down. After release and removal of the beam 12 from the chamber 3, the entire equipment is carried out of the area of the installation and subjected, as far as possible, to decontamination. Also the control console 32 is moved out of the area of the installation.

In other words, the primary carriage 19 is releasably connected with the guide conduit 18 and threaded drive shaft 28, so it can be removed from the beam 12, the latter and this carriage being then individually transversely compact enough for passage through the manhole 9. Although not shown, the primary carriage may have a hook connection with the guide conduit 18, which is secure when the primary carriage is horizontal, this carriage resting on the threaded drive shaft 28 via a threaded rest to strut and thereby hold this cantilever carriage horizontal. Upward swinging of this carriage then permits its release from the beam 12.

What is claimed is:

1. An apparatus for use with a pressurized-water reactor's steam generator having a manifold chamber enclosing the bottom side of a horizontal tube sheet having holes therethrough in which are mounted the tubes of a heat exchanger tube bundle which extends upwardly from the tube sheet's top side, said chamber having a manhole giving access to said tube sheet's bottom side to permit internal inspection or repair of said tubes by registration of an end of a flexible guide conduit with said holes and through which a flexible carrier can be guided for insertion via said holes through the tubes extending from the tube sheet's other side; said apparatus including a fixture insertable through said access opening and comprising a beam, means for detachably supporting said beam horizontally in said chamber beneath said tube sheet's bottom side, a horizontal cantilever arm having one end provided with means for supporting said guide conduit with its end pointing upwardly, and means for mounting the other end of said arm on one side of said beam and means for horizontally moving the end of said arm having said supporting means relative to said beam, whereby said guide conduit may be aligned with said holes in said tube sheet.

2. The apparatus of claim 1 in which said beam has a longitudinal guideway, a primary cantilever carriage having one end mounted by said guideway to travel therealong, said carriage extending transversely from said beam and having a longitudinal guideway extending therealong transversely with respect to said beam's guideway, and a secondary carriage mounted by said carriage's guideway to travel therealong and rotatively mounting said arm's said other end to form its said mounting means with said arm's said one end having said conduit supporting means, swinging horizontally to register with said holes.

3. The apparatus of claim 2 including remotely controlled motors respectively connected to move said primary and secondary carriages along the guideways by which they are mounted and to pivotally swing said arm's end having said conduit supporting means.

4. The apparatus of claim 3 having means for orienting said beam in said chamber when supported therein so that operation of said motors by programming causes them to move said carriages and swing said arm's end having said conduit supporting means to positions registering the latter with any selected one of said tube sheet holes.

5. The apparatus of claim 4 in which said beams said supporting and said orienting means respectively comprise means on the opposite ends of said beam for releasably pressing against opposite insides of said chamber, and positioning pins extending upwardly from said beam for insertion into holes in the bottom side of said tube sheet.

6. The apparatus of claim 4 including a flexible guide conduit having an inner end supported by said conduit supporting means on said arm's said end which swings, said conduit being long enough to extend therefrom through said access opening to an outer end at a location outside thereof, and means at said location for mounting a coil of flexible carrier hose having an end for carrying tube interior inspection and repairing devices, said hose being long enough to extend from said location into various locations in the heat exchanger tube in which it may be inserted and having an inside through which signals and power may be transmitted.

7. The apparatus of claim 4 including flexible power conductors connected individually with each of said motors and extending therefrom through said access opening to a location relatively remote therefrom, and means at said location for controllably powering said motors individually via said conductors.

8. The apparatus of claim 6 in which means are provided for transmitting signals via said hose's interior to said location for obtaining data via said signal transmitting means.

9. An apparatus for use with a pressurized-water reactor's steam generator having a manifold chamber enclosing a first side of a tube sheet having holes therethrough in which are mounted the tubes of a heat exchanger tube bundle which extends from the tube sheet's second side, said chamber having a manhole giving access to said tube sheet's first side to permit internal inspection or repair of said tubes by registration of an end of a flexible guide conduit with said holes and through which a flexible carrier can be guided for insertion via said holes through the tubes extending from the tube sheet's second side; said apparatus including a fixture insertable through said access opening and comprising a beam, means for detachably supporting said beam in said chamber near said tube sheet's first side, a cantilever arm having one end provided with means for supporting said guide conduit with its end pointing towards the tube sheet, and means for mounting the other end of said arm on one side of said beam and means for horizontally moving the end of said arm having said supporting means relative to said beam, whereby said guide conduit may be aligned with said holes in said tube sheet.

* * * * *

UNITED STATES PATENT AND TRADEMARK OFFICE
CERTIFICATE OF CORRECTION

PATENT NO. : 3 934 731
DATED : January 27, 1976
INVENTOR(S) : Otto Müller et al

It is certified that error appears in the above-identified patent and that said Letters Patent are hereby corrected as shown below:

Foreign Application Priority Data, change No. "2264143" to "2263143."

Column 5, line 8, change "of" (second occurrence) to "to".

*Signed and Sealed this*

*fourth* Day of *May 1976*

[SEAL]

Attest:

RUTH C. MASON
*Attesting Officer*

C. MARSHALL DANN
*Commissioner of Patents and Trademarks*